United States Patent [19]

Mueller, deceased et al.

[11] Patent Number: 4,996,872

[45] Date of Patent: Mar. 5, 1991

[54] MODULAR CORE HOLDER

[75] Inventors: James Mueller, deceased, late of Duncan, by Grace Mueller, executrix; Clinton W. Cole; Syed Hamid, both of Duncan; Jackie K. Lucas, Marlow, all of Okla.

[73] Assignee: Halliburton Company, Duncan, Okla.

[21] Appl. No.: 467,110

[22] Filed: Jan. 18, 1990

[51] Int. Cl.$^5$ ............................................. G01N 15/08
[52] U.S. Cl. ...................................................... 73/38
[58] Field of Search ............................................. 73/38

[56] References Cited

U.S. PATENT DOCUMENTS 4,868,751 9/1989 Dogru et al. ........................ 73/30 X

FOREIGN PATENT DOCUMENTS 794434 1/1981 U.S.S.R. ................................... 73/38

OTHER PUBLICATIONS

A Temco, Inc. Catalog entry for an "Incremental Pressure Core Holder, DCH Series", dated at least one year prior to 1/4/90.
A Temco, Inc. catalog entry for a "Medium Pressure Permeability Core Holder, RCH Series", dated 6/3/82.
A Temco, Inc. catalog entry for a "High Pressure Permeability Core Holder, HCH-4", dated 5/12/82.
A Temco, Inc. catalog entry for a "Medium Pressure Core Holder, RCH Series", dated 6/3/82.
A Temco, Inc. catalog entry for a "High Pressure Permeability Core Holder, HCH Series", dated 12/6/82.
A Temco, Inc. catalog entry for "core Holders For Permeability Testing, MCH-1 Series", dated 10/1/81.
A Temco, Inc. catalog entry for a "Resistivity Core Holder, ECH Series", dated 8/83.
Exhibit 1—drawing of device believed to have been publicly or commercially—disclosed or used more than one year before 1/4/90.

Primary Examiner—Hezron E. Williams
Assistant Examiner—Joseph W. Roskos
Attorney, Agent, or Firm—James R. Duzan; E. Harrison Gilbert, III

[57] ABSTRACT

A core holder for testing core permeability includes a modular sleeve comprising a series of sleeve segments aligned longitudinally. Port rings positioned between the sleeve segments have radial holes to allow conditions within the core-receiving cavity formed by the sleeve segments and the port rings to be monitored from outside the core holder. The port rings and the sleeve segments are disposed within a housing, and spacer rings are received about the sleeve segments to support the sleeve segments and port rings within the housing. Conditions within the modular sleeve may be monitored through instruments connected to holes in the housing communicating with the holes in the port rings.

20 Claims, 3 Drawing Sheets

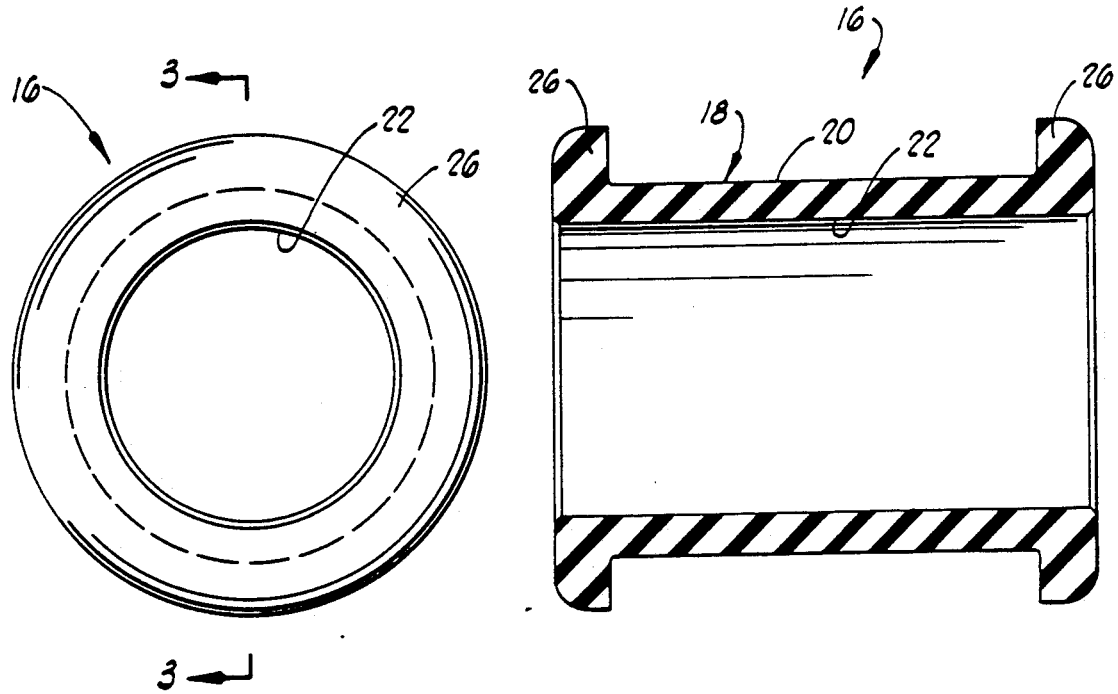
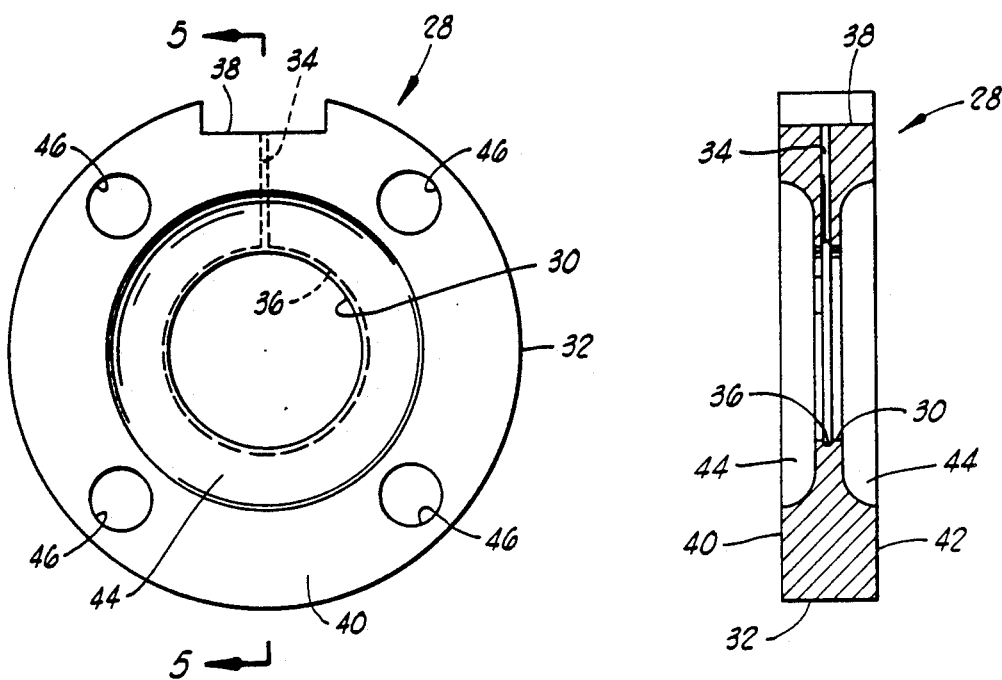

MODULAR CORE HOLDER

BACKGROUND OF THE INVENTION

The present invention generally relates to core holders used in testing core samples, and more particularly to a core holder utilizing a modular sleeve.

In geological exploration, the physical characteristics of an underground formation are of paramount importance. Permeability, a measure of resistance to fluid flow, is a particularly important factor that affects the method of oil recovery to be used for a particular well.

To determine permeability, a core sample is removed from the underground formation. The core sample is placed in a core holder, where it is subjected to heat and pressure conditions comparable to those underground. Fluid is then forced through the core sample at high pressure. The permeability of the core is indicated by the change in pressure at various points along the length of the core.

During testing, the core is encased in a rubber sleeve. Because pressure measurements must be taken at various points along the core's length, pressure taps must be provided. In at least one type of sleeve, the taps are molded directly into the rubber sleeve. Such a sleeve with integral pressure taps is relatively expensive.

The conditions involved in core testing cause the rubber sleeve to deteriorate rapidly. A core, and its encasing sleeve, may be subjected to pressures greater than 10,000 pounds per square inch, and temperatures near 400° F., for example. When testing under these conditions, the rubber sleeve may have to be replaced after every test.

Conventional core holders accommodate sleeves of a certain length. If a core to be tested is too long for the sleeve, a core holder with a longer sleeve must be used. As a result, core holders of various sizes are frequently maintained in the same laboratory. Because each core holder demands its own supply of sleeves, a great variety of sleeves of different lengths must be manufactured and kept in stock.

Therefore, there is a need for a core holder using a sleeve that does not require pressure taps molded into the material so that each sleeve is relatively less expensive, and that can be used with different lengths of cores so that an inventory of different length sleeves is not required.

SUMMARY OF THE INVENTION

The present invention overcomes the above-noted and other shortcomings of the prior art by providing a novel and improved core holder.

The present invention removes the necessity for pressure taps to be molded into the sleeve, thus reducing the manufacturing cost.

Further, the present invention permits the sleeve length to be varied without changing the manufacturing process of the sleeves and without requiring an inventory of sleeves of different lengths.

Also, the present invention provides a novel means for permitting pressure within the sleeve to be measured.

The present invention provides a modular core holder comprising a sleeve, forming an internal cavity for receiving a core, the sleeve including a plurality of segments; support means, overlying the sleeve, for supporting the sleeve; and access means, positioned between at least two of the segments of the sleeve, for allowing measurement of conditions within the internal cavity.

In a preferred embodiment, the support means includes a housing; and a plurality of spacer rings, disposed within the housing and overlying the segments, for supporting the segments within the housing.

In a preferred embodiment, the access means includes a port ring positioned between two sleeve segments. The port ring has a radial hole communicating with an inner circumferential groove for pressure communication from around a circumference of the core under test.

In a preferred embodiment, the modular core holder further comprises means for applying a compressive force to the spacer rings so that the spacer rings urge flanges of the sleeve segments against the port ring.

Therefore, from the foregoing, it is a general object of the present invention to provide a novel and improved modular core holder. Other and further objects, features and advantages of the present invention will readily be apparent to those skilled in the art when the following description of the preferred embodiment is read in conjunction with the accompanying drawings.

BRIEF DESCRIPTION OF THE DRAWINGS

FIG. 2 is an end view of a sleeve segment of the modular core holder shown in FIG. 1.

FIG. 3 is a cross-sectional view of the sleeve segment as taken along line 3—3 shown in FIG. 2.

FIG. 4 is an end view of a port ring of the modular core holder shown in FIG. 1.

FIG. 5 is a cross-sectional view of the port ring as taken along line 5—5 shown in FIG. 4.

DETAILED DESCRIPTION OF THE PREFERRED EMBODIMENT

The present invention provides a modular core holder for testing the characteristics of a core. In its preferred embodiment shown in FIG. 1, the invention is a core holder 12 suitable for testing cores under high pressure and high temperature conditions.

Figure 1:
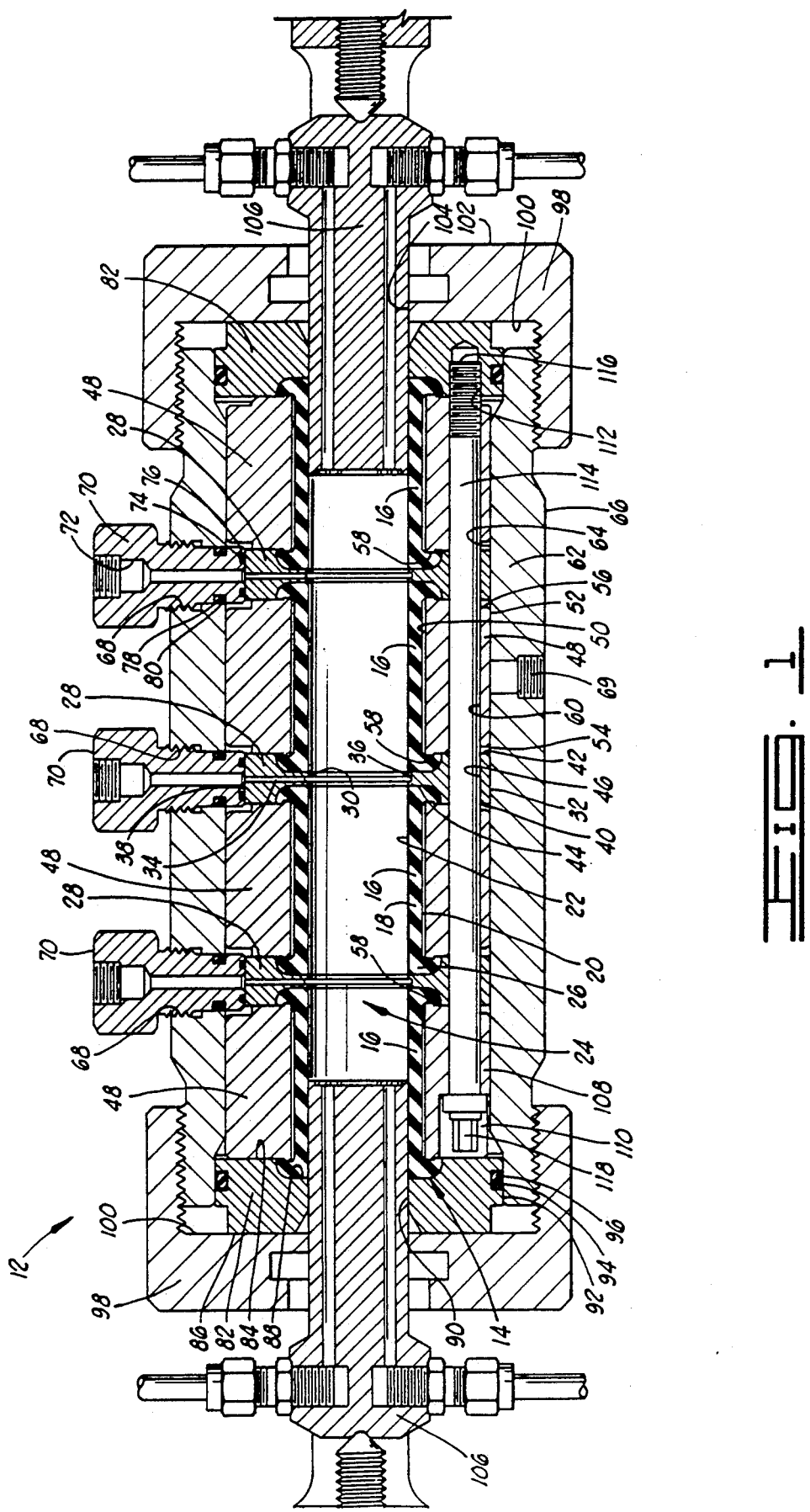
FIG. 1 is a cross-sectional view of a preferred embodiment modular core holder of the present invention.

The core holder 12 includes a segmented sleeve 14. The sleeve 14 includes at least two discrete resilient cylindrical sleeve segments 16 aligned longitudinally. Referring to FIGS. 2 and 3, each sleeve segment 16 comprises a tubular central portion 18 having an outer surface 20, and an inner surface 22 defining part of an internal cavity 24 (FIG. 1). Each sleeve segment 16 also has an annular resilient flange 26 extending radially from each end of the tubular portion 18. The inner surface 22 extends 5 through the flanges 26. Each flange 26 is a sealing member which seals against an adjacent structure under compressive loading as will be further described hereinbelow.

A respective port ring 28 (FIGS. 1, 4 and 5) is positioned between each pair of adjacent sleeve segments 16. Each port ring 28 includes an inner surface 30 defining part of the internal cavity 24. The surfaces 30 are aligned with the surfaces 22 of the sleeve segments 16. Each port ring 28 further includes an outer surface 32 from which a cylindrical surface defining a radial hole 34 extends inward to the inner surface 30 so that the hole 34 communicates conditions inside the cavity 24 to outside the port ring 28. The inner surface 30 of the port ring 28 has an annular inner circumferential groove 36 which intersects the radial hole 34 so that pressure from around a circumference of the core under test is communicated to the radial hole 34. The outer surface 32 of the port ring 28 includes a flat surface 38 surrounding the radial hole 34. Each port ring 28 further includes two sides 40, 42 each of which has an annular groove 44 to receive one of the flanges 26 of the adjacent sleeve segment 16. The sides 40, 42 extend radially between the cylindrical surfaces 30, 32. Each port ring 28 includes four longitudinal holes 46 (one shown in FIG. 1) extending through both sides 40, 42.

With the port rings 28 positioned between the sleeve segments 16, as shown in FIG. 1, the surfaces 22, 30 define the cavity 24. The cavity 24 receives the core to be tested, while conditions within the cavity 24 can be monitored by instruments communicating with the radial holes 34 in the port rings 28. Thus, access to the cavity 24 for allowing measurement of conditions within the cavity 24 is through the port rings 28, not through the integral bodies of the sleeve segments 16.

Figure 6:
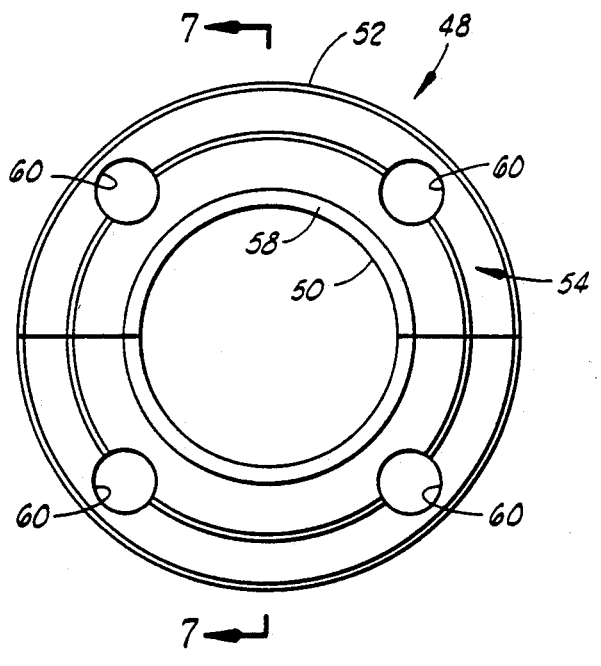
FIG. 6 is an end view of a spacer ring of the modular core holder shown in FIG. 1.
Figure 7:
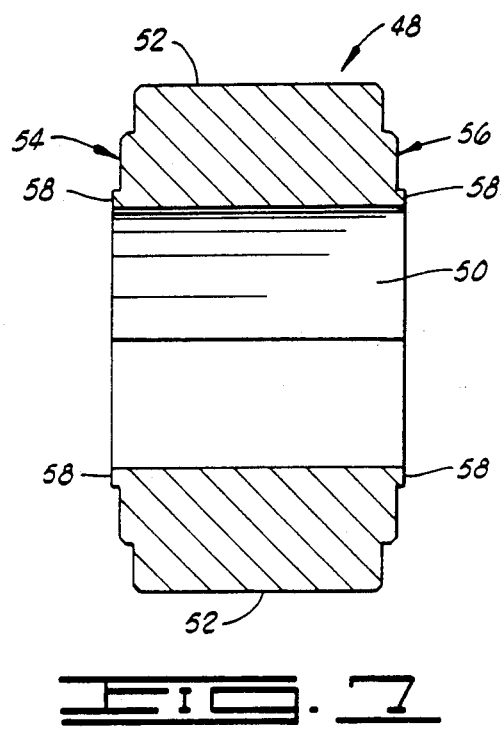
FIG. 7 is a cross-sectional view of the spacer ring as taken along line 7—7 shown in FIG. 6.

Each of the sleeve segments 16 receives a spacer ring 48 (FIGS. 1, 6 and 7) about its outer surface 20 between its flanges 26. Each spacer ring 48 includes a cylindrical inner surface 50 next to the cylindrical outer surface 20 of the respective sleeve segment 16. Each spacer ring 48 also includes a cylindrical outer surface 52. Each spacer ring 48 further comprises two radial ends 54, 56, which for interior spacer rings are next to radial sides 42, 40 of adjacent port rings 28. Each spacer ring 48 also includes an annular member 58 protruding from each end 54, 56 of the spacer ring 48. Upon application of a compressive force, the annular protuberance 58 engages the adjacent flange 26 of the respective sleeve segment 16, thereby urging the resilient flange 26 against the port ring 28 to form a seal between the sleeve segment 16 and the respective radial side of the port ring 28. In addition, each spacer ring 48 has four longitudinal holes 60 (one shown in FIG. 1) formed between the two ends 54, 56 of the spacer ring 48. The longitudinal holes 60 in the spacer rings 48 are aligned with the longitudinal holes 46 in the adjacent port rings 28. Each spacer ring 48 is split longitudinally into halves to allow the spacer ring 48 to be placed around, in concentric overlying relation with, the respective sleeve segment 16 during assembly.

The sleeve segments 16, port rings 28 and spacer rings 48 are assembled as shown in FIG. 1. The desired number of sleeve segments 16 are selected, and facing flanged ends of consecutive segments 16 are placed in opposing annular grooves 44 of a respective port ring 28. The spacer rings 48 are placed around the sleeve segments 16 so that holes 60 in the spacer rings 48 align with holes 46 in the port rings 28. Bolts passed through the aligned holes 60, 46 and connected to a seal cap, subsequently described more particularly, secure the assembly with a compressive force which holds the flanges 26 of the sleeve segments 16 sealingly against the adjacent port rings 28.

The assembly is retained in a conventional core holder housing. The housing includes a cylindrical body or container 62 having an inner surface 64 adjacent the outer surfaces 32 of the port rings 28 and the outer surfaces 52 of the spacer rings 48. The body 62 includes an outer surface 66 from which at least one hole 68 and a hole 69 extend radially inward through the wall of the body 62 to the inner surface 64.

Each such hole 68 is aligned with a respective one of the radial ports 34 of the port rings 28. A conventional tap 70 is disposed through each such hole 68 if desired. The tap 70 includes a longitudinal hole 72, which communicates with the aligned radial hole 34 in the port ring 28. The portion of the tap 70 outside the housing body 62 is formed to allow conventional pressure measuring instruments to be attached to the longitudinal hole 72 in a known manner. The portion of the tap 70 inside the housing body 62 abuts the flat surface 38 of the respective port ring 28, and has an annular groove 74 which receives an O-ring 76, forming a seal between the tap 70 and the port ring 28. The tap's outer surface also has a circumferential groove 78 which receives an O-ring 80, forming a seal between the tap 70 and the housing body 62 within the hole 68. Through the tap 70, conditions within the cavity 24 of the core holder 12 can be monitored by conventional external equipment known in the art.

The housing also includes end caps 98 threadedly attached to each end of the housing body 62. Each end cap 98 has two sides 100, 102. Each end cap 98 further includes an inner surface 104 defining a hole in the center of the end cap 98 for receiving apertured plugs 106 through which the pressurized and heated fluid used in testing are input and output as known in the art. The pressure of the fluid input through the plugs 106 is less than a pressure applied through the hole 69 of the body 62 so that the pressure differential effects a seal around a core located in the cavity 24. This prevents leakage around the circumference of the core, which otherwise would result in the measurement of higher-than-actual core permeability.

A respective annular seal cap 82 is disposed within each end of the housing. Each seal cap 82 includes two sides 84, 86. The side 84 abuts the adjacent sleeve segment 16 and spacer ring 48 at a respective end of the cavity 24. The side 84 also has an annular groove 88 for receiving the flange 26 at that end of the adjacent sleeve segment 16. The side 86 abuts the side 100 of the adjacent housing end cap 98 when the end cap is fastened down on the housing body 62. Each seal cap 82 includes an inner surface 90 defining a hole in the center of the seal cap 82, and an outer surface 92 abutting the inner surface 64 of the housing body 62. The outer surface 92 has an annular groove 94 which receives an O-ring 96, forming a seal between the seal cap 82 and the housing body 62.

Figure 8:
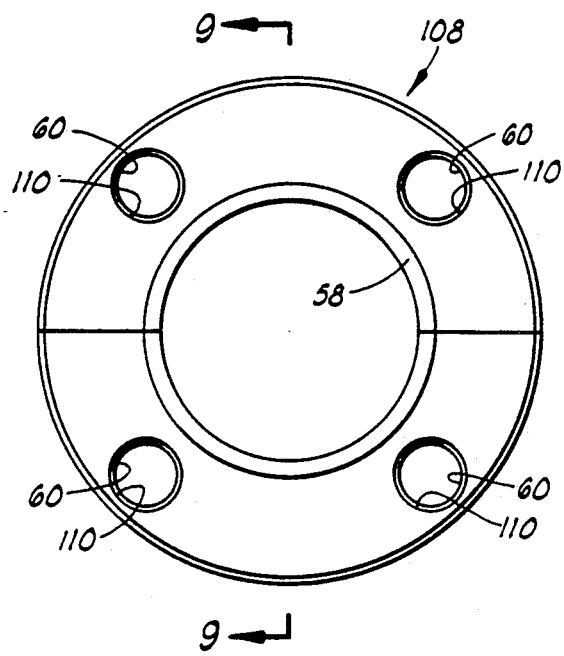
FIG. 8 is an end view of a bolt-end spacer ring of the modular core holder shown in FIG. 1.
Figure 9:
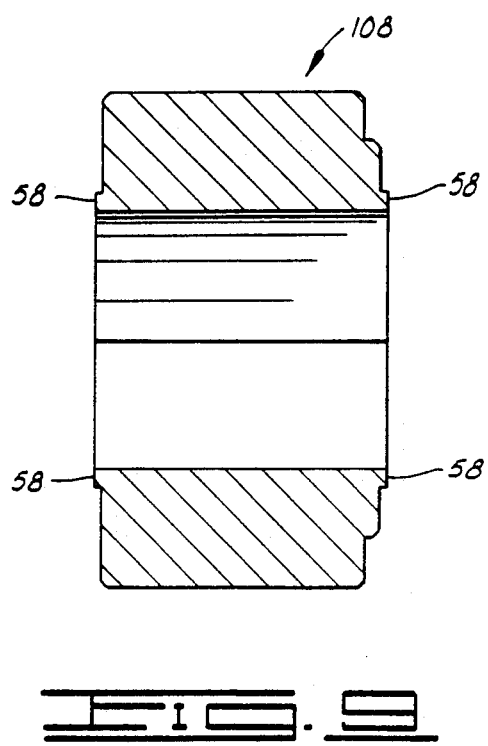
FIG. 9 is a cross-sectional view of the bolt-end spacer ring as taken along line 9—9 shown in FIG. 8.

In FIG. 1, the left-most spacer ring 48 may be referred to as a bolt-end spacer ring which is also marked with the reference numeral 108 (see also FIGS. 8 and 9). This spacer ring 108 has one end the same as the other spacer rings 48, but its other end is flat but for the protuberance 58 and an enlarged void 110 at the end of each of the longitudinal holes 60 so that the void 110 receives the head of a bolt 114. The seal cap 82 at the end of the cavity 24 opposite the end spacer ring 108 also includes four threaded holes 112 aligned with the longitudinal holes 60 in the adjacent spacer ring 48. Four bolts 114 are received through the holes 60 in the spacer rings 48, 108 and the holes 46 in the port rings 28. A first end 116 of each of the bolts 114 threadingly engages a respective one of the threaded holes 112 in the seal cap 82 at the end opposite the spacer ring 108. A second end 118 of each of the bolts 114 has a head which is seated in the respective void 110 in the spacer ring 108. The bolts 114 are tightened to apply a compressive force to the spacer rings 48, the port rings 28, and the flanges 26, thereby ensuring positive sealing between the flanges 26 and the port rings 28.

The spacer rings, the housing, the seal caps and the bolts are constituents of a support means for supporting the sleeve segments and the port rings.

Thus, the present invention provides a core holder using a modular sleeve to avoid the need for access taps to be integral in a unitary sleeve. This reduces cost and the diversity of inventory required. Accordingly, the present invention is well adapted to carry out the objects and attain the ends and advantages mentioned above as well as those inherent therein. While a preferred embodiment of the invention has been described for the purpose of this disclosure, changes in the construction and arrangement of parts can be made by those skilled in the art, which changes are encompassed within the spirit of this invention as defined by the appended claims.

What is claimed is:

1. A modular core holder, comprising:
   a sleeve, forming an internal cavity for receiving a core, said sleeve including a plurality of segments;
   support means, overlying said sleeve, for supporting said sleeve; and
   access means, positioned between at least two of said segments of said sleeve, for allowing measurement of conditions within said internal cavity.

2. A modular core holder as defined in claim 1, wherein said support means includes:
   a housing; and
   a plurality of spacer rings, disposed within said housing and overlying said segments, for supporting said segments within said housing.

3. A modular core holder as defined in claim 1, wherein:
   said support means includes a wall having a hole defined therein; and
   said access means includes a member having a hole defined therein for allowing measurement of conditions within said internal cavity from said hole in said support means.

4. A modular core holder as defined in claim 1, wherein each of said segments includes a sealing member associated with an end of said segment.

5. A modular core holder as defined in claim 4, wherein said support means includes:
   a housing; and
   a plurality of spacer rings, disposed within said housing and overlying said segments, for supporting said segments within said housing.

6. A modular core holder as defined in claim 5, wherein;
   said housing includes a wall having a hole defined therein; and
   said access means includes a member having a hole defined therein for allowing measurement of conditions within said internal cavity from said hole in said housing.

7. A modular core holder, comprising:
   two sleeve segments defining at least part of a cavity for receiving a core to be tested under heat and pressure; and
   a port ring positioned between said two sleeve segments for allowing measurement of conditions within said cavity.

8. A modular core holder as defined in claim 7, wherein said port ring includes a side defining an annular groove for receiving an end of one of said sleeve segments.

9. A modular core holder as defined in claim 7, wherein each of said sleeve segments includes:
   a cylindrical tube formed of resilient material; and
   seal means associated with an end of said tube for providing a seal between said port ring and said tube.

10. A modular core holder as defined in claim 9, wherein said seal means includes an annular resilient flange extending radially from an end of said tube.

11. A modular core holder as defined in claim 10, further comprising two spacer rings, each of said spacer rings received about a respective one of said tubes and each of said spacer rings having at least one end from which an annular member protrudes for engaging and urging a respective one of said flanges of the respective one of said tubes against said port ring.

12. A modular core holder as defined in claim 7, wherein said port ring includes;
    an inner circumferential surface;
    an outer circumferential surface positioned radially outward from said inner surface; and
    a surface defining a radial hole between said inner surface and said outer circumferential surfaces.

13. A modular core holder as defined in claim 12, wherein said inner surface defines an annular circumferential groove so that said groove intersects said radial hole in said port ring.

14. A modular core holder as defined in claim 7, further comprising two spacer rings, concentrically overlying said two sleeve segments and engaging said port ring, for supporting said two sleeve segments.

15. A modular core holder as defined in claim 14, wherein:
    said port ring has a longitudinal hole defined therethrough;
    each of said spacer rings has a longitudinal hole defined therethrough; and
    said modular core holder further comprises:
       a housing overlying said sleeve segments, said port ring, and said spacer rings;
       a seal cap disposed within and engaging said housing and abutting one of said sleeve segments and one of said spacer rings, said seal cap having a threaded hole defined therein; and
       a bolt disposed through said longitudinal hole in said port ring and said longitudinal holes in said spacer rings and securely engaging said threaded hole in said seal cap so that a compressive force is applied to said port ring and said spacer rings.

16. A modular core holder as defined in claim 15, wherein one of said spacer rings is an end spacer ring having a void defined at an end of said longitudinal hole thereof for receiving a head of said bolt.

17. A modular core holder as defined in claim 15, wherein said seal cap includes:
    an outer surface defining a groove for receiving a sealing member for sealingly engaging said housing; and
    a side extending radially inward from said outer surface, said side having an annular groove defined therein for receiving an end of said one of said sleeve segments.

18. A modular core holder as defined in claim 15, wherein said housing includes:
- a cylindrical container having a hole defined therein;
- an end cap, attached to an end of said container; and
- a tap, disposed through said hole in said container, for communicating conditions within said cavity from said port ring to a measurement instrument.

19. A modular core holder, comprising:
- a cylindrical housing;
- two cylindrical, resilient sleeve segments aligned longitudinally and disposed within said housing, wherein each of said sleeve segments includes:
  - a central portion including:
    - an outer surface; and
    - an inner surface defining a cavity; and two end portions, each disposed at a respective end of said central portion of said sleeve and each including an annular, resilient flange extending radially from a respective end of said central portion, wherein said inner surface defining said cavity extends through said two end portions;
- a port ring, disposed within said housing and between said two sleeve segments, including:
  - an inner circumferential surface having an annular groove defined therein;
  - a surface defining a hole extending radially outward from said inner surface in communication with said groove; and
  - two sides, extending radially outward from said inner surface, each of said sides having an annular groove defined therein for receiving one of said flanges of a respective one of said sleeve segments; and
- two spacer rings, each of which is disposed within said housing and overlying said outer surface of one of said sleeve segments and abutting one of said sides of said port ring.

20. A modular core holder as defined in claim 19, further comprising means for applying a compressive force to said spacer rings so that said spacer rings urge said flanges of said sleeve segments received by said port ring against said port ring.

* * * * *